(12) United States Patent
El-Atab et al.

(10) Patent No.: US 11,307,191 B2
(45) Date of Patent: Apr. 19, 2022

(54) MULTI-DIMENSIONAL INTEGRATED CIRCUIT FOR REAL-TIME MONITORING OF A FLUIDIC ENVIRONMENT

(71) Applicant: KING ABDULLAH UNIVERSITY OF SCIENCE AND TECHNOLOGY, Thuwal (SA)

(72) Inventors: Nazek Mohamad El-Atab, Thuwal (SA); Muhammad Mustafa Hussain, Hercules, CA (US)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 0 days.

(21) Appl. No.: 16/993,746

(22) Filed: Aug. 14, 2020

(65) Prior Publication Data

US 2021/0055278 A1 Feb. 25, 2021

Related U.S. Application Data

(60) Provisional application No. 62/890,160, filed on Aug. 22, 2019.

(51) Int. Cl.
G01N 33/18 (2006.01)
(52) U.S. Cl.
CPC .................... *G01N 33/18* (2013.01)

(58) Field of Classification Search
CPC .................................................. G01N 33/18
See application file for complete search history.

(56) References Cited

U.S. PATENT DOCUMENTS

| 2006/0292043 A1* | 12/2006 | Biberger | G01N 33/18 |
| | | | 73/53.01 |
| 2017/0098361 A1* | 4/2017 | Sentosa | G01N 33/18 |
| 2019/0257807 A1* | 8/2019 | Witelson | G01N 33/1826 |

* cited by examiner

*Primary Examiner* — Natalie Huls
*Assistant Examiner* — Cynthia L. Davis
(74) *Attorney, Agent, or Firm* — Patent Portfolio Builders PLLC

(57) ABSTRACT

A multi-dimensional integrated circuit (MD-IC) device for monitoring one or more parameters of a fluid includes plural faces, each face having plural interlocks extending from a periphery of the face for interlocking with corresponding interlocks of another face of the plural faces; the plural faces are mechanically attached to each other and electrically connected through the interlocks to form a closed chamber; an energy harvester placed on an outside surface of a first face of the plural faces; a fluidic monitoring sensor placed on an outside surface of a second face of the plural faces; a processor placed within the closed chamber; and a battery placed within the closed chamber and configured to receive the electrical energy from the energy harvester and to provide the electrical energy to the processor and the water monitoring sensor.

20 Claims, 15 Drawing Sheets

FIG. 2

MULTI-DIMENSIONAL INTEGRATED CIRCUIT FOR REAL-TIME MONITORING OF A FLUIDIC ENVIRONMENT

CROSS-REFERENCE TO RELATED APPLICATIONS

This application claims priority to U.S. Provisional Patent Application No. 62/890,160, filed on Aug. 22, 2019, entitled "MULTI-DIMENSIONAL INTEGRATED CIRCUIT FOR WATER AND FOOD SECURITY," the disclosure of which is incorporated herein by reference in its entirety.

BACKGROUND

Technical Field

Embodiments of the subject matter disclosed herein generally relate to a system for monitoring the quality of a given fluidic environment, and more particularly, to a multi-dimensional, integrated circuit that is configured to collect information while embedded in the given environment, and transmit it in a wireless manner to an operator of the environment.

Discussion of the Background

Commercial systems for observing the water quality in ponds used for growing the fish do exist. However, the existing systems can monitor one characteristic at a time such as conductivity meters, ammonia sensors, oxygen meters, etc. This approach is considered as an expensive and time consuming solution for the farmer. Moreover, the commercially available and previously reported IoT multi-sensory systems for water monitoring are bulky, expensive and require installation by the experts. In addition, the existing systems either are not capable of automatically transmitting the data to the operator of the pond, or require a power source that needs to be charged or replaced.

Thus, there is a need for a new system that is capable of automatically collecting all the necessary information for monitoring the pond and the wellbeing of the culture in the pond, automatically transmitting this information, in a wireless manner, to the operator of the pond, providing a continuous source of energy that does not need to be replaced or recharged, and also offering this system at a low price and with a small footprint so that it is affordable for the farmers.

BRIEF SUMMARY OF THE INVENTION

According to an embodiment, there is a multi-dimensional integrated circuit (MD-IC) device for monitoring one or more parameters of a fluid. The system includes plural faces, each face having plural interlocks on a periphery for interlocking with corresponding interlocks of another face of the plural faces; the plural faces are mechanically attached to each other through the interlocks to form a closed chamber; an energy harvester placed on an outside surface of a first face of the plural faces, so that the energy harvester converts solar energy into electrical energy; a fluidic monitoring sensor placed on an outside surface of a second face of the plural faces, so that the fluidic monitoring sensor monitors the one or more parameters of the fluid; a processor placed within the closed chamber; and a battery placed within the closed chamber and configured to receive the electrical energy from the energy harvester and to provide the electrical energy to the processor and the water monitoring sensor.

According to another embodiment, there is a multi-dimensional integrated circuit (MD-IC) device for monitoring one or more parameters in a fluid, and the system includes plural faces, each face having plural interlocks on a periphery for interlocking with corresponding interlocks of another face of the plural faces; the plural faces are attached to each other through the interlocks to form a closed chamber; an energy harvester is placed on an outside surface of a first face of the plural faces, so that the energy harvester converts solar energy into electrical energy; a fluidic monitoring sensor is placed on an outside surface of a second face of the plural faces, so that the fluidic monitoring sensor monitors the one or more parameters of the fluid; an air monitoring sensor is placed on an outside surface of a third face of the plural faces, so that the air monitoring sensor monitors an air parameter, wherein the third face is mechanically connected to both the first face and the second face; and a polymer layer externally covering connections between the plural faces to seal the closed chamber from ambient. The polymer layer on the second face is thicker than on the first and third faces so that the third face is a bottom face and stays in contact with the fluid, the first face is a top face and exposes the energy harvester to sun, and the third face is a side face that exposes the air monitoring sensors to air.

According to yet another embodiment, there is a method of manufacturing a multi-dimensional integrated circuit (MD-IC) device that monitors one or more parameters in a fluid. The method includes providing plural faces, each face having plural interlocks on a periphery for interlocking with corresponding interlocks of another face of the plural faces; placing an energy harvester on an outside surface of a first face of the plural faces, so that the energy harvester converts solar energy into electrical energy; placing a fluidic monitoring sensor on an outside surface of a second face of the plural faces, so that the fluidic monitoring sensor monitors the one or more parameters of the fluid; placing a processor on an inside surface of a face of the plural faces; placing a battery on an inside surface of another face of the plural faces, wherein the battery is configured to receive the electrical energy from the energy harvester and to provide the electrical energy to the processor and the fluidic monitoring sensor; placing an air monitoring sensor on an outside surface of a third face of the plural faces, so that the air monitoring sensor monitors an air parameter; directly attaching each face of the plural faces to at least three other faces with the interlocks to form a closed chamber; and sealing each connection between any two faces with a polymer layer to seal the closed chamber from an ambient.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a cubic device that is directly deployed in the water for collecting the necessary data. However, the embodiments to be discussed next are not limited to a cubic device, but they may be applied to devices having different shapes and the device may be deployed in any fluid to monitor the parameters of that fluid.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a small and lightweight device, using a multi-dimensional integrated circuit (MD-IC), is configured for direct deployment in a pond for monitoring the water in the fish farming pond. The MD-IC technology used to make the MD-IC device merges the benefits of the two most successful integration and packaging technologies: system-on-chip (SoC) and system-in-package (SiP). In fact, the MD-IC device introduced herein exceeds the restricted functionalities of the SoC technology and the bulky dimensions and inefficient area consumption of the SiP approach. The cubic MD-IC device includes thin-film based sensors on its outer sides for simultaneous air and water quality monitoring while data management circuitry and a solid state battery are integrated on its internal sides, all of which are electrically and mechanically interconnected using through-silicon-vias (TSVs) and side interlocks. The integrated system is then encapsulated using a polymeric material to waterproof the embedded microcontroller and battery, improve the mechanical robustness of the system and enable it to float on the surface of the water for solar energy harvesting and wireless data transfer. A Bluetooth low energy unit (BLE) and light emitting diodes (LEDs) are provided on the device to offer the farmer fast and real-time water monitoring results. In one application, silicon solar cells are embedded in the MD-IC device for achieving a complete, compact-packaged, lightweight and high performance multi-sensory system for water and food security applications.

Figure 1:
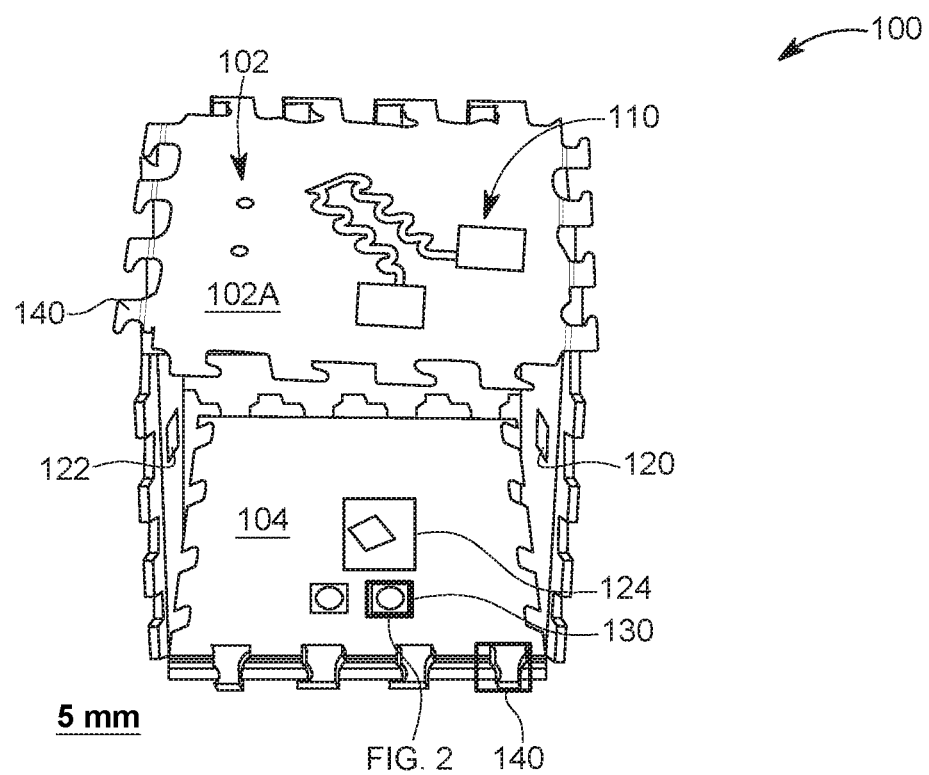
FIG. 1 is a schematic diagram of a multi-dimensional integrated circuit (MD-IC) device that is configured to float in water while monitoring water and/or air parameters.

The manufacturing of a MD-IC device 100, which is shown in FIG. 1, is realized using a CMOS based processes. The MD-IC device 100 has one or more water monitoring sensors 110 located on the outside surface 102A of one or more faces 102 of the device. While FIG. 1 shows a cubic MD-IC device 100, other shapes may be used. The faces 102 define an internal chamber 104. A battery 120 may be located on an inside surface 102B of the one or more faces 102 of the cube, i.e., inside the chamber 104. In addition, a memory 122 and a microprocessor 124 may also be located on the inside surface 102G of the one or more faces 102, also inside the chamber 104. As discussed later, the chamber 104 is sealed so that no water or even air from outside the device enters inside the chamber. In this way, all the electronic components located inside the chamber are protected from the ambient. The battery, memory and the microprocessor may be located on the same inside surface or on multiple inside surfaces of the chamber. Moreover, the sealing allows the system to float on the water.

Figure 2:
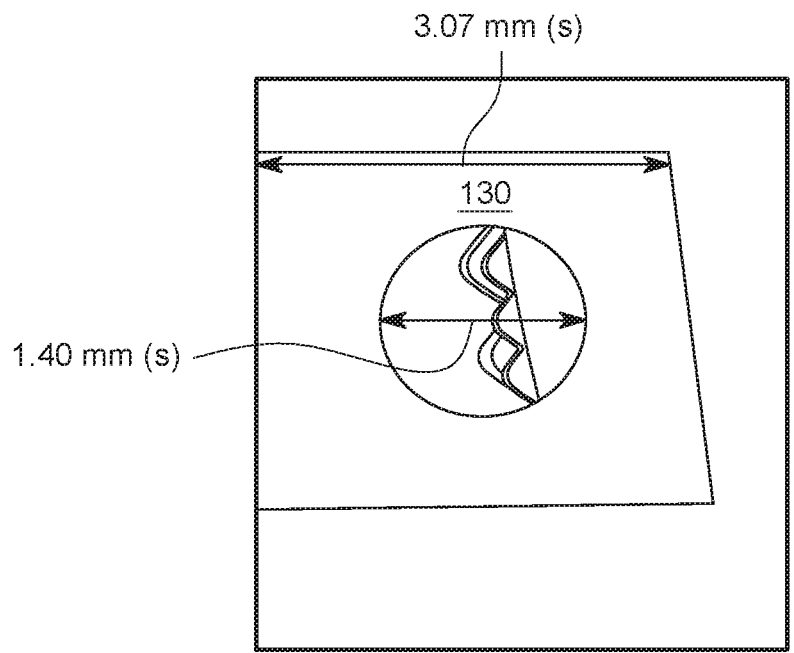
FIG. 2 shows a detailed view of an electrical contact between an external surface and an internal surface of a same face of the MD-IC device.

To achieve electrical communication between the elements disposed on the inside surface of a face and the elements disposed on the outside surface of the same face, one or more through-silicon-vias 130 are made. The details of a single through-silicon-via 130 are shown in FIG. 2 together with exemplary sizes of such element. To ensure that signals and/or energy can be transmitted between two elements that are located on different faces of the cube, plural interlocks 140 are made on the periphery of each face, as shown in FIG. 1.

Figure 3:
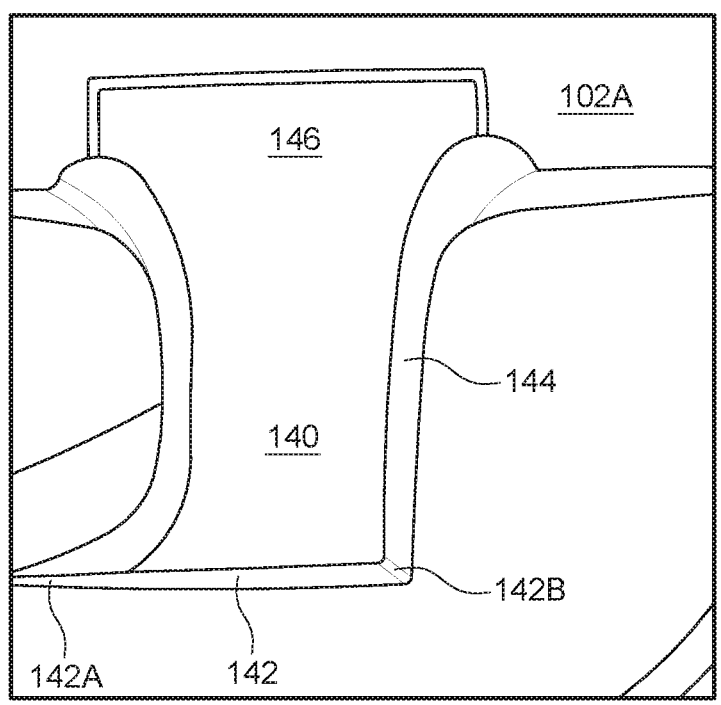
FIG. 3 shows a detailed view of an interlock that is part of a face of the MD-IC device and is used for mechanically and electrically connecting the faces of the device to each other.

An interlock 140 is shown in FIG. 3 extending from the face 102. Note that the interlock 140 has a head 142, distal from the face 102, that is configured to engage with a corresponding interlock from an adjacent face so that the two faces are mechanically locked together, as shown in FIG. 1. The head 142 may be configured to have sharp end 142A and a flat end 142B for better engagement with other interlocks and also for preventing the separation of the interlocks when the faces are connected to each other. The interlock 140 also has a body 144, and a base 146 that is integrally made with the face 102. In one embodiment, each face has plural interlocks, for example, between 10 and 100, uniformly distributed on its perimeter. The interlocks 140 may be made of an insulator material, similar to the material of the face 102, for example Si. However, one or more interlocks 140 are then metalized so that an electrical connection is achieved between the interlock of one face and the corresponding interlock of an adjacent face, to achieve electrical communication between different elements located on two adjacent faces.

Figure 4A:
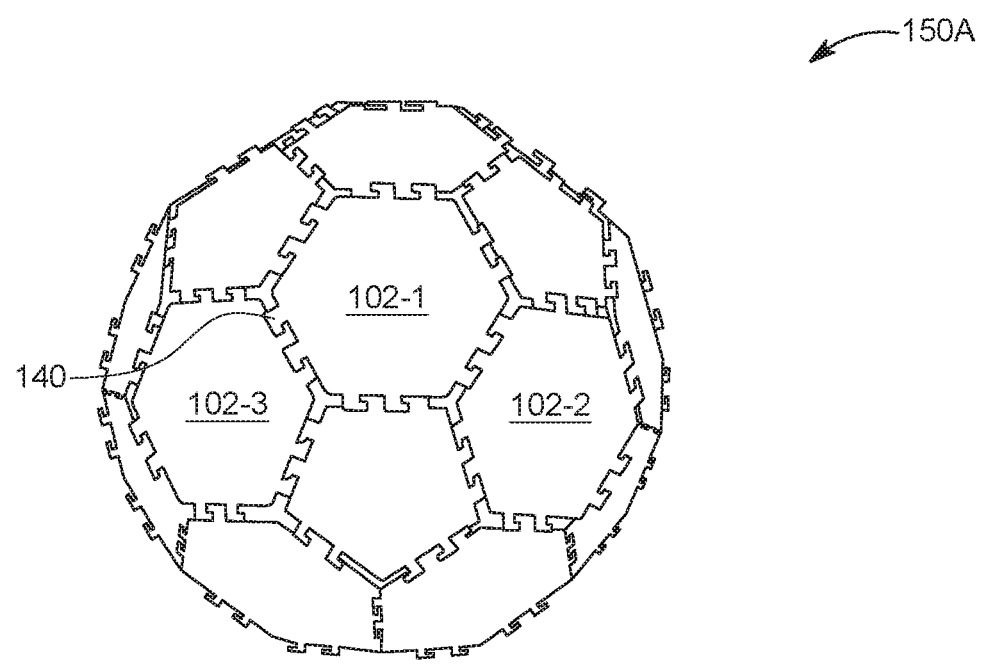
FIGS. 4A to 4D show the MD-IC device having different shapes and/or sizes.
Figure 4B:
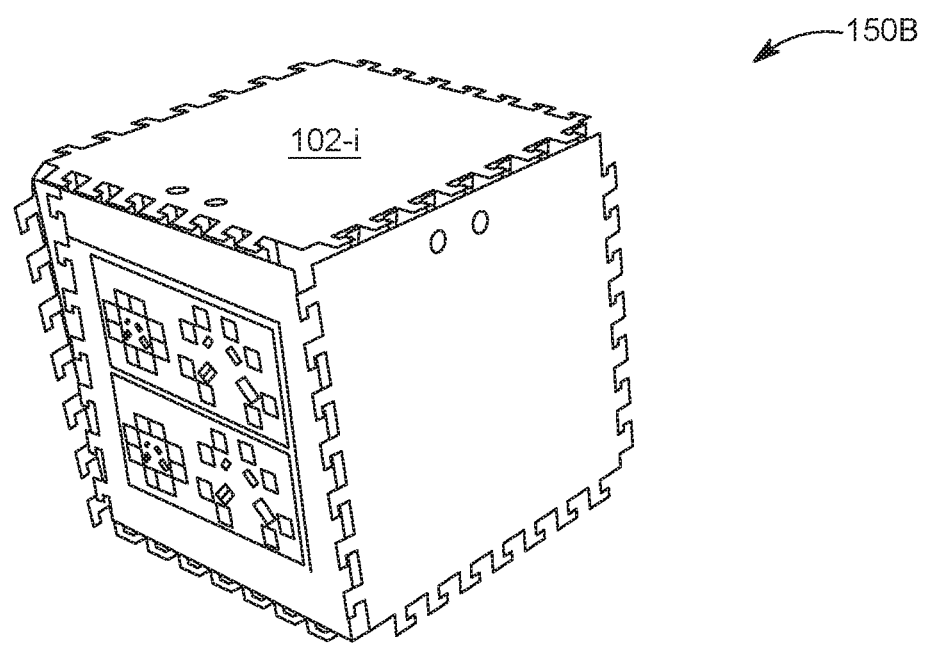
Figure 4C:
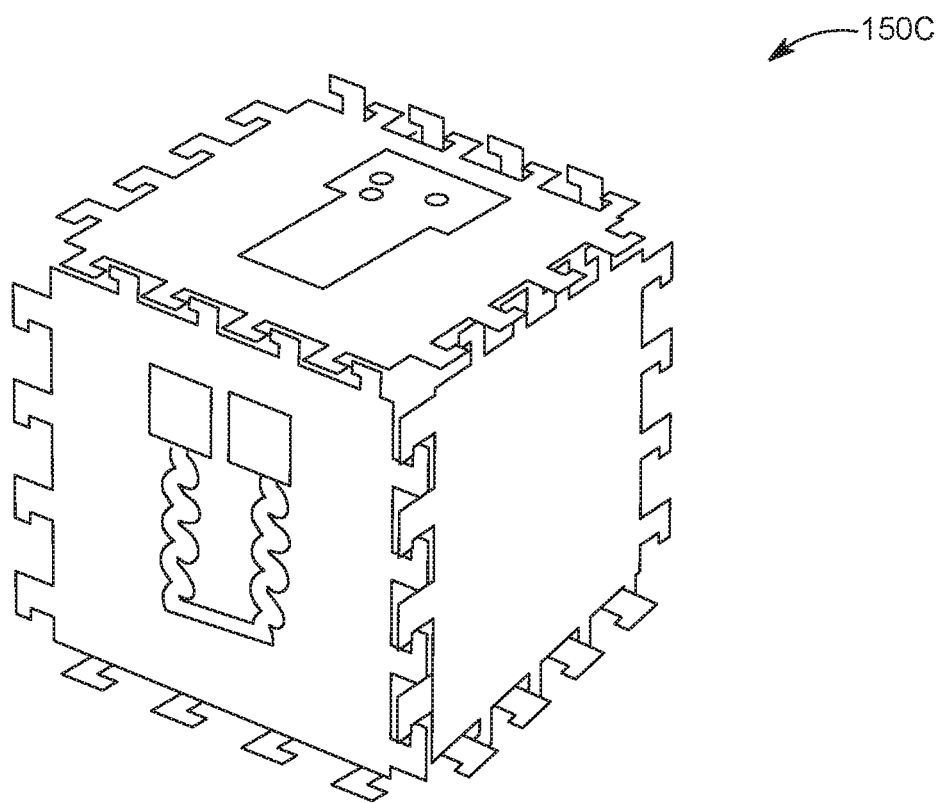
Figure 4D:
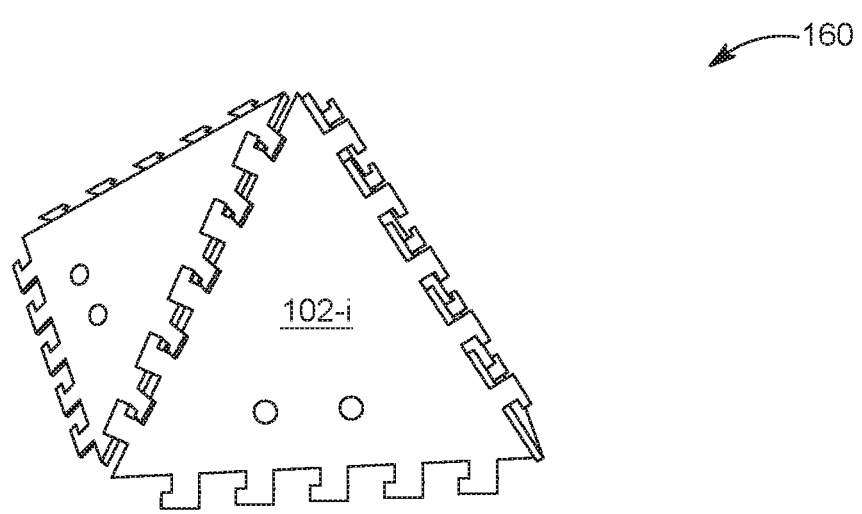

FIG. 4A shows a spherical MD-IC device 150A having plural faces 102-i, with i being an integer equal to or larger than 5, mechanically and electrically interconnected to each through the interlocks 140. A diameter of the device 150A is about 10 cm in FIG. 4A. However, other sizes may be used. FIG. 4B shows a cubic MD-IC device 150B having a size of about 4 cm, FIG. 4C shows a cubic MD-IC device 150C having a size of about 2 cm, and FIG. 4D shows a pyramidal MD-IC device 160 having a size of about 3 cm. Other shapes and sizes may be used for forming the MD-IC devices 100, 150A to 150C, and 160.

Figure 5:
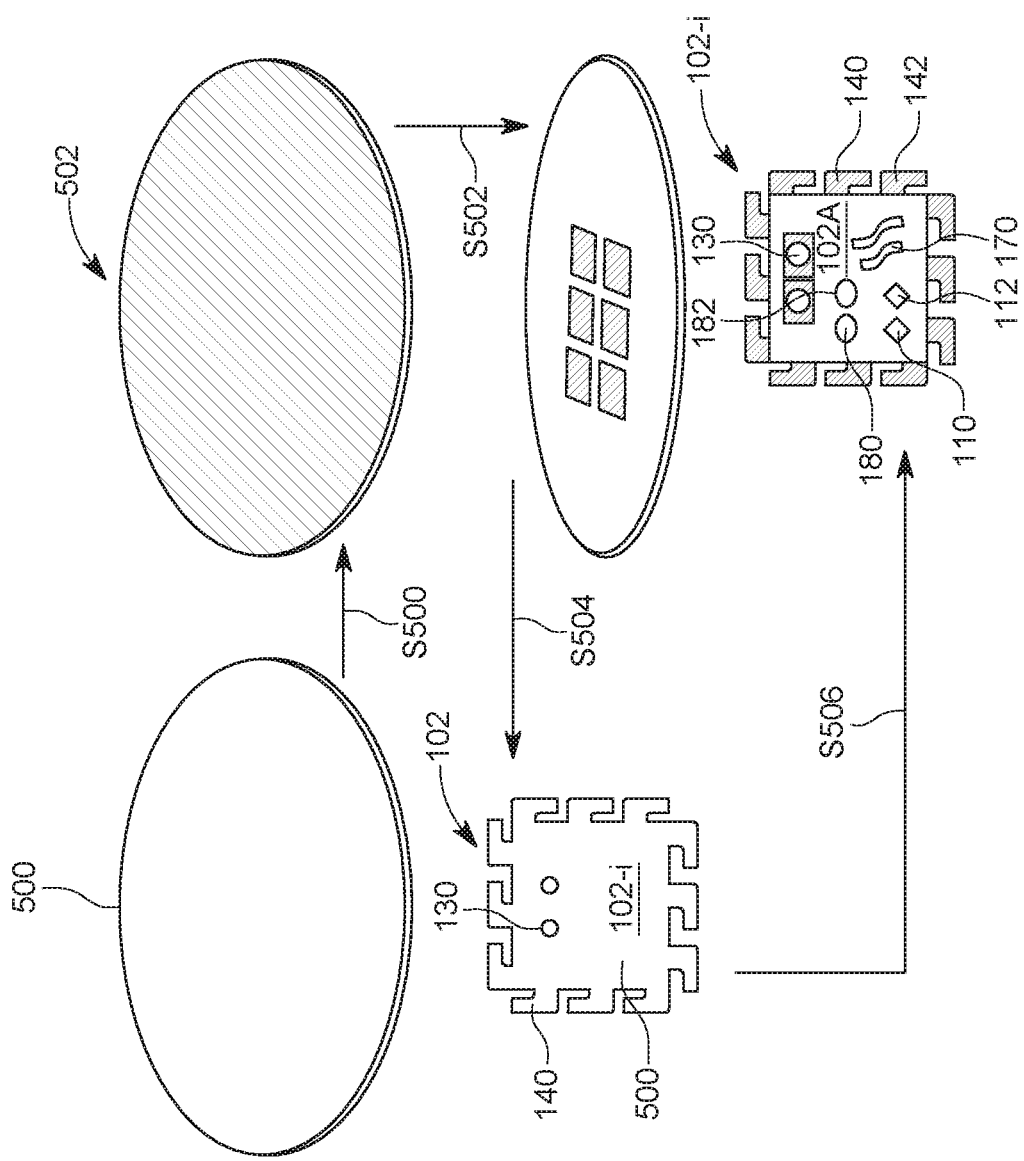
FIG. 5 schematically illustrates a process for manufacturing a face of the MD-IC device.

In one application, the plural faces 102-i of the MD-IC device 100 are fabricated using $CO_2$ laser patterning followed by silicon deep reactive ion etching (DRIE) Bosch process etching, as schematically illustrated in FIG. 5. The process starts with a substrate 500 (e.g., Si substrate) on which a photoresist 502 and a polymer (e.g., Kapton polymer) is added in step S500. Next, the $CO_2$ laser is used for patterning the photoresist 502 in step S502 and then the exposed areas are completely removed via a Bosh process etching in step S504, in an Oxford deep reactive ion etching (DRIE) tool with sulfur hexafluoride ($SF_6$) and carbon fluoride ($C_4F_6$). Other etching techniques could be used as well. The obtained isolated sides are immersed in acetone to lift off the kapton, and the interconnects are e-beam evaporated with 500-nm silver. Different metal deposition techniques could be used as well. The DRIE process is also used for making the interlocks 140 and for shaping the substrate to obtain the desired size for each face 102-i.

Next, in step S506, one or more thin-film sensors 110 and metal interconnects 142 are formed on both sides of the face 102-i and/or the interlocks 140 with the existing methods. In one application, an air sensor 112 may be formed. In another application, an antenna 170 may also be formed on the external surface 102A of the face 102-i. In this application or another application, an energy harvester 180, for example, a solar panel, may be placed on the external surface 102A for collecting solar energy and providing electrical energy to the battery and/or the other elements of the device. In addition, it is possible to also place one or more LED lights 182 on the external surface 102A of the face 102-i, for transmitting visual signals to the operator of the pond in which the device 100 is provided.

In the following examples, various sensor fabrication and integration methods into the MD-IC device are explained. More specifically, the $SiO_2$ film 500 with 300-nm thickness is grown using an Oxford plasma enhanced chemical vapor deposition (PECVD) system on the Si substrate. Next, 10 nm/180 nm Ti/Au is sputtered. A temperature detectors are patterned by photolithography and RIE-based etching. A graphene monolayer is synthesized on copper foil using a chemical vapor deposition system and is then transferred onto the silicon substrate by first etching the copper using $FeCl_3$ for 24 hours. The graphene is next immersed in deionized water and scooped on the metallic electrodes of the pH detector. The monolayer is then left to dry at ambient conditions for 24 hours. A salinity sensor is fabricated by sputtering 200-nm platinum and patterning interdigitated electrodes using photolithography. An ammonia sensor is based on 3D graphene foam which is induced by $CO_2$ laser ablating a polyimide sheet and transferred onto the PDMS. The ammonia sensor is a two terminal device, the resistance change is extracted by applying a 0.6 V and reading the output current. The antenna is fabricated by first sputtering 200-nm copper on a ring-patterned photoresist using photolithography followed by lift off. The photovoltaic device 180 uses monocrystalline Si and tin coated copper interdigitated back electrodes. On the internal faces of the cubic system, a microcontroller chip (pre-fabricated bare-die) is integrated in addition to a solid-state battery (micro-lithium-ion based).

The sensor 110 may be any one of a temperature sensor, which is based on standard resistive temperature detection (RTD), a humidity/pressure/PH level sensor that uses interdigitated electrodes and a graphene monolayer as the sensing medium, a salinity sensor, which is based on interdigitated electrodes, and an ammonia sensor, which uses a 3D graphene foam with a high surface area-to-volume ratio as the sensing medium. Any combination of these sensors may be placed on any face of the device 100. In one application, each face hosts the same combination of sensors. In another application, each face hosts a different sensor. In still another application, each face hosts a combination of these sensors. In one embodiment, a graphene based on-chip RF system can also be included in the MD-IC device and graphene-based storage devices. The solar cell may be based on crystalline Si cells with interdigitated back contacts, and the antenna may be based on a copper ring structure. The number of interlocks and TSVs, size of the MD-IC device and shape can be customized according to the application requirements, i.e., depending on the size of the fish, the size of the pond, the parameters that need to be monitored, etc.

While the elements shown in FIG. 5 may be disposed on the same face 102 of the device 100, in one application, it is possible to have the solar panel 180 covering an entire face, another face to be covered by the antenna 170, still another face to be covered only with one or more water monitoring sensors 110, another face covered only with air monitoring sensors 112, and yet another face to be covered only with LEDs 182. In another configuration, these elements may be combined in any desired manner on one or more of the faces of the device 100.

As previously discussed, every MD-IC device face includes multiple metal-coated interlocks 140 to electrically interconnect to the neighboring faces in a puzzle-like fashion. In addition, the TSVs 130 connect the top and bottom sides (inner and outer sides) of each MD-IC face. Electronic devices that necessitate active materials other than Si can be integrated on the unpolished side of the substrate, while data management devices could be integrated on the polished Si face with lower defects density. In one application, the MD-IC device 100 enables the integration of heterogeneous materials, i.e., a Ge or GaSb substrate could be used for one face for the fabrication of higher efficiency III-V solar cells instead of the silicon substrate used for another face. The MD-IC will thus not be limited by the restriction of a common wafer process as in SoC, instead, optimized thin-film based devices can be integrated into the system i.e., a GaAs heterojunction bipolar transistor RF can be integrated in one package with III-V solar cells on Ge substrate and sensors on Si. This technology becomes even more promising with the advent of the bio-electronic systems, where microfluidic devices are integrated with bio-sensing components, wireless components, and control electronics.

In terms of scalability, the MD-IC device 100's size can be scaled up or down according to the application requirements. Cubic MD-ICs devices have been fabricated with different sizes: 4-cm, 2-cm, 1.5-cm, 8-mm, and 5-mm sides which can be smaller than the size of a medical pill. In fact, the MD-IC device can also be employed in biomedical applications as implantable/injectable microsystems. In addition, the capability to scale down the MD-IC device and therefore to pack heterogeneous and high-performance sensors, communication systems and processors into millimeter-sized cubes makes the proposed integration scheme suitable for refining the performance of "smart dust" devices.

Figure 6:
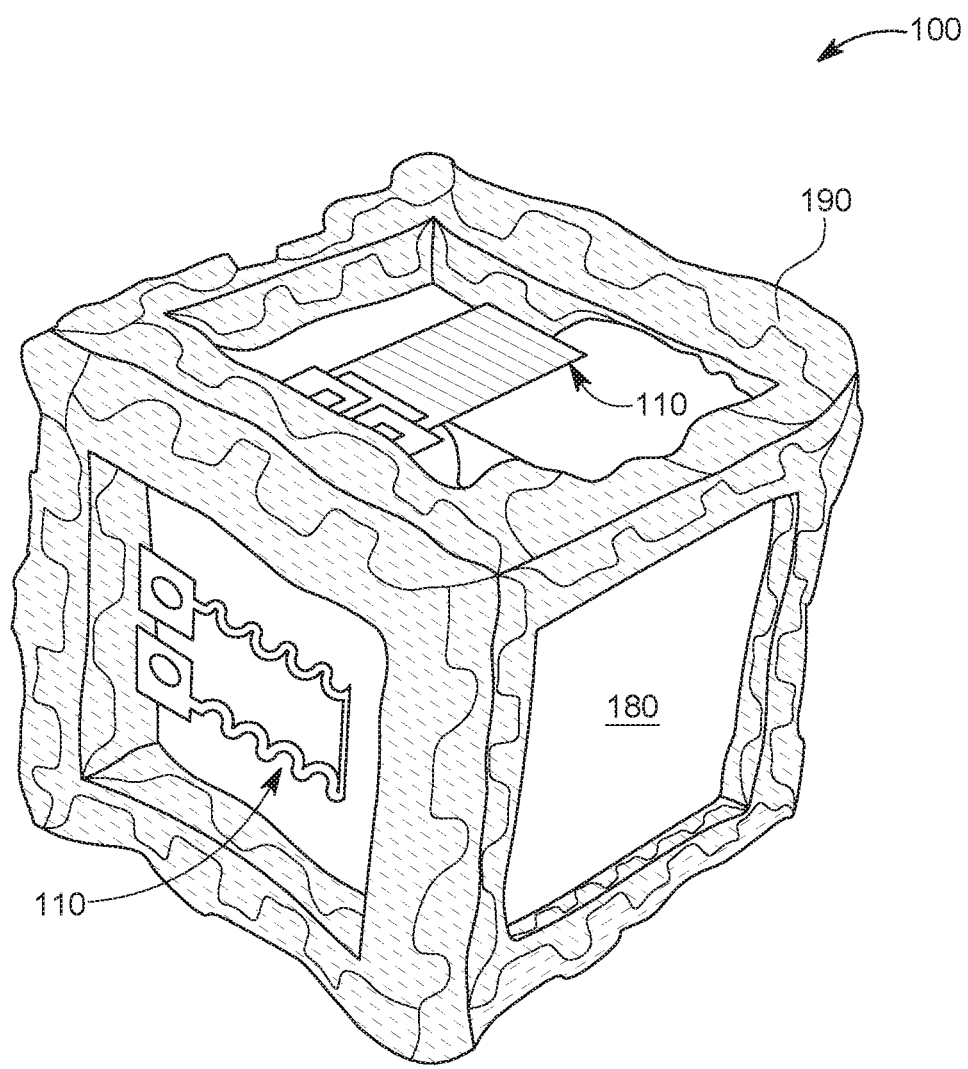
FIG. 6 shows the MD-IC device after a polymer layer is added to seal an internal chamber and enable the floating mechanism.

The MD-IC device 100 interlocks 140 are encapsulated in a bio-friendly polymer, for example, by using Poly-dimethylsiloxane (PDMS) layer 190, as shown in FIG. 6, to isolate/seal the inside circuitry of the chamber 104 from the outside environment. In this way, the chamber 104 is sealed from the ambient. The PDMS is arranged by mixing 1:10 PDMS curing agent: silicone elastomer followed by degassing in a vacuum mixer for 4 minutes at a 1.1 kPa pressure with a speed of 700 rpm to get rid of any trapped air. The cubic system is next covered with the encapsulant and cured at a temperature of 60° C. for 24 hrs. The MD-IC device may be encapsulated with 6 layers of PDMS to make sure that there are no defects in the encapsulation that could lead to the leakage of water from the fish farming pond into the MD-IC device. Other polymers could also be used.

Figure 8:
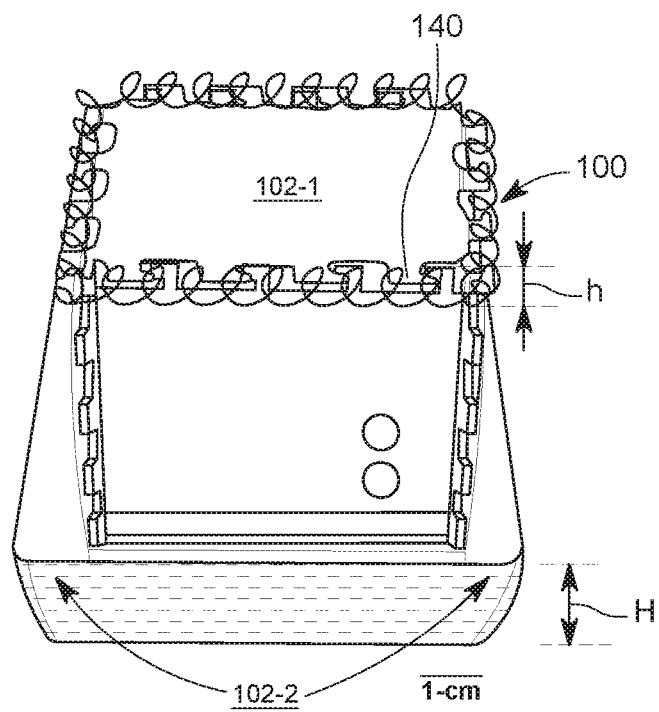
FIG. 8 shows the MD-IC device having the polymer layer coated with a higher thickness (asymmetrical) on the base face of the device than on the other faces to ensure that the device always floats on the same face.

To make an asymmetric PDMS encapsulation, the cubic system is placed in a Poly(methyl methacrylate) (PMMA) based mold with a depth of 6 mm. Six layers of PDMS are then poured onto the cubic system and cured at 60° C. for 24 hrs. Once cured, the bottom PDMS with 6 mm thickness is cut in an asymmetric way as shown in FIG. 8 (wider PDMS on the left side) such that the weight is distributed asymmetrically. This ensures that the system will always flip such that the heaviest side (with thickest PDMS) will be at the bottom and in contact with water. The design of the encapsulation could be changed depending on the application requirements.

FIG. 6 also show the MD-I device 100 having a solar panel 180 occupying an entire face of the cube, a first sensor 110 on one face and a second sensor 110 on another face. The PDMS on the outer sides of the MD-IC device is then patterned to keep the outer electronic components (i.e., sensors 110, 112, solar cell 180, antenna 170, etc.) exposed to the external environment.

Figure 7:
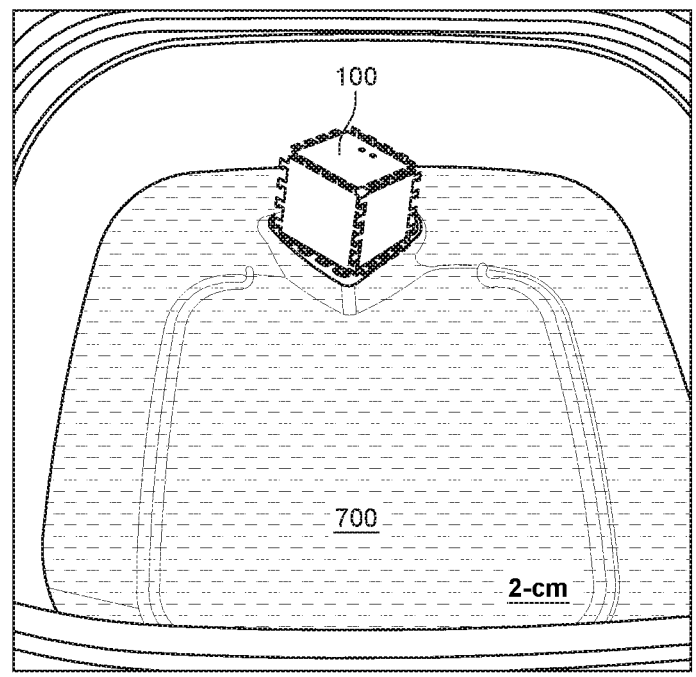
FIG. 7 shows the MD-IC device floating in water.

The MD-IC device 100 is configured to float on the surface of the water for several reasons: 1) to monitor the quality of the water and air simultaneously, 2) to harvest solar energy, and 3) to enable simple and real-time wireless transfer of data to the operator of the pond. The PDMS that completely encapsulates the MD-IC device makes the device 100 to be less dense than the water due to the inner trapped air, and as a result, it floats on the surface of the water 700, as shown in FIG. 7. In one embodiment, the MD-IC device 100 includes a single face with embedded water quality sensors, thus, whenever an external force (e.g., contact with fishes) causes the rotation of the cubic system 100, this face needs to flip back to the original position such that the desired face is in contact with the water. The remaining outer faces can include thin-film based air quality sensors 112 in addition to the energy harvesting devices and antenna. To achieve this positioning of the device 100, the PDMS 190 around the side with the water sensors (bottom face 102-2) is made thicker and asymmetric, as shown in FIG. 8, which would shift the center of gravity of the MD-IC device downward and achieve a stable equilibrium when the desired face 102-2 is immersed in water. The design of the encapsulated MD-IC could be changed based on the application requirements, for example, if the MD-IC device is required to be fully immersed in water and not floating, the trapped air would be removed to enable the immersion of the system.

Figure 9A:
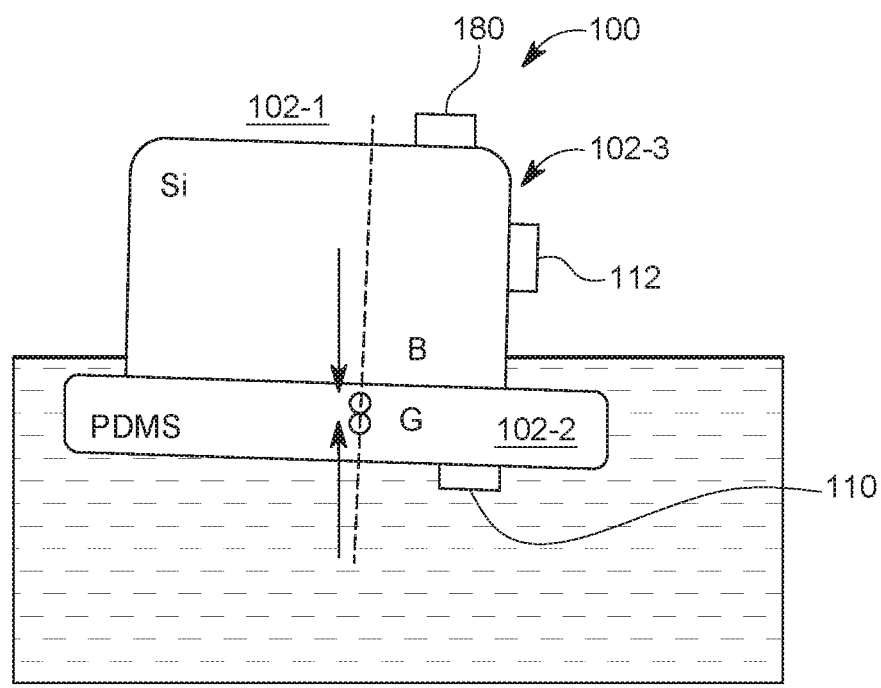
FIGS. 9A and 9B schematically illustrate the forces acting on the MD-IC device due to the thick polymer layer formed on the bottom face.

FIG. 8 shows the surface 102-1 being a top surface and the surface 102-2 being a bottom surface. The PDMS layer 190 has a thickness H on the bottom face that is larger than a thickness h of the PDMS layer on any of the interlocks 140. The floating mechanism of the MD-IC device 100, when under mechanical perturbations, is now explained using the governing fluid mechanics. The basic principle to determine whether a body will float or sink over a fluid depends on the opposite forces acting on it. The MD-IC device 100 is subjected to two forces called the gravitational force (downward force due to its weight) and up-thrust force or buoyancy force exerted by the liquid, as shown in FIG. 9A. If the gravitational force (G) is smaller than the buoyancy force (B), the body would float. In fact, Archimedes' principle claims that any immersed or floating body is lifted up by a force that is equivalent to the weight of the displaced water. The line of action of force of buoyancy is called center of buoyancy. Therefore, the body will keep floating in a stable state if B exceeds or becomes equal to G of the body.

Figure 9B:
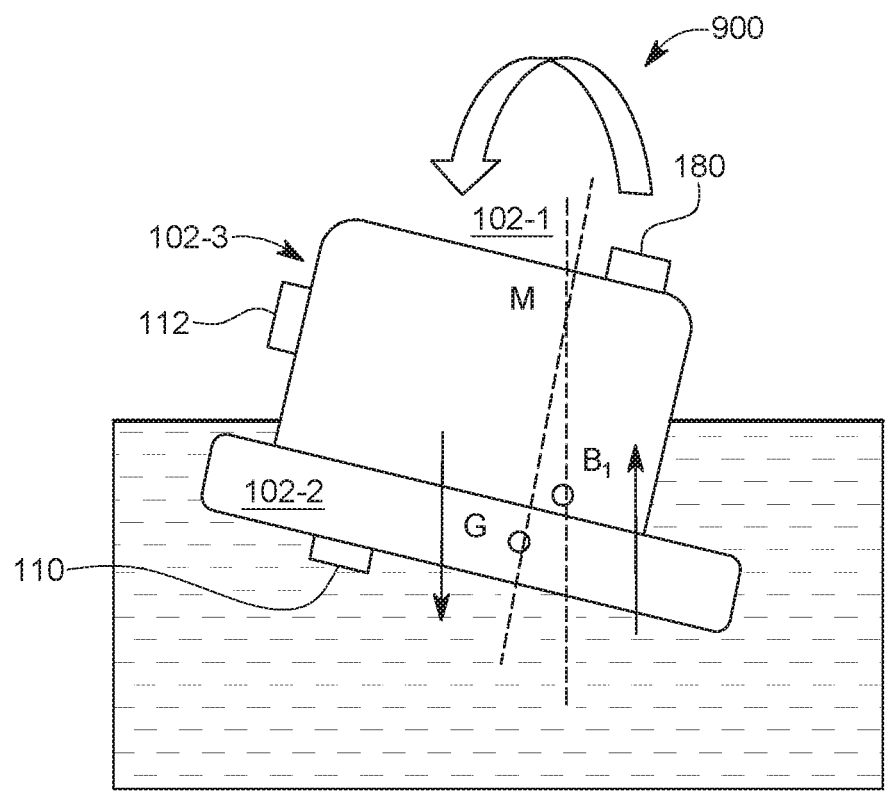

When the body oscillates or experiences mechanical perturbations, as illustrated in FIG. 9B, it alters the total volume of the displaced water i.e., changes the original B position to a new position called Bi, however, G remains at the same position, as shown in FIG. 9B. The intersection of the line passing through the original G and B and the line passing through the new point Bi (orthogonally to the water line) is called the metacenter height (M). It is possible to control the response of the floating body by looking at the value of M, i.e., whether it will return to its original position or not. The larger the M value is (M is positive), the more stable it will be and would readily return to its initial position due to returning moment.

Thus, to make the MD-IC device 100 stable during the floating phase (i.e. stabilize its position), the G of the system is shifted from the centroid of the body by making the base 102-2 heavier as compared to the upper body using the thicker PDMS 190 encapsulation shown in FIG. 8. As a result, the G of the MD-IC device is shifted downward (i.e., G is below B), thus making the MD-IC device always stable. Therefore, when the body of the device 100 is subjected to mechanical perturbations, the heavy base 102-2 creates a restoring moment 900 that returns the MD-IC device to its original position. Additionally, the off-center location of the G is used by providing the asymmetry to ensure that the system will always assume the preferred position in the water even when the system is rotated by 180°. This means that the operator of the pond can simply throw the device 100 into the water for deployment, and the device will orient itself to have the bottom face 102-2 in the water and the upper face 102-1 to face toward the sun. Thus, for this embodiment, the solar panel is placed on the top face 102-1 and the water monitoring sensors are placed on the bottom face 102-2. The air monitoring sensors 112, which may have the same configuration as the water monitoring sensors 110, may be placed on a lateral face 102-3 as, shown in FIGS. 9A and 9B. As a result, the farmer can easily deploy the cubic system by simply throwing it into the pond water, the MD-IC device 100 will then autonomously adjust its orientation owing to the PDMS encapsulation design.

In another embodiment, the problem of orienting the MD-IC device 100 when thrown into the water may be circumvented by making all the faces of the device have the same configuration in terms of the sensors and other elements. In other words, each face has the same sensor configuration and distribution, the same solar panel, and antenna, so that, no matter how the device lands into the water, a face having the solar panel is always a top surface, and a face having the water monitoring sensors is always a bottom face. The processor may be configured to detect which face is in water, using the humidity sensor, and then to consider only the readings from that face as being associated with the water measurements, and the readings from the opposite face as being associated with the air measurements.

As previously discussed, the PDMS layer 190 is patterned using the $CO_2$ laser to expose the active area of the different sensors to the outer environment, and thus to be in direct contact with the water/air ambient. In addition, the encapsulation of the MD-IC device enhances the mechanical robustness of the system by absorbing any mechanical shock and protects the embedded electronics such as the solar cell and the microcontroller due to its water resistant characteristic. In this regard, note that the optimum depth of fish farming ponds is around 2 m and that the required oxygen level in the water is usually maintained by using different aerators such as waterfalls or spitters in the ponds. These aerators contribute to the mixing of the water and reducing the inhomogeneity in water properties throughout the pond. Therefore, even though the MD-IC device 100 is floating on the surface of the water, it can provide reliable measurements of the water properties throughout the pond.

Figure 10:
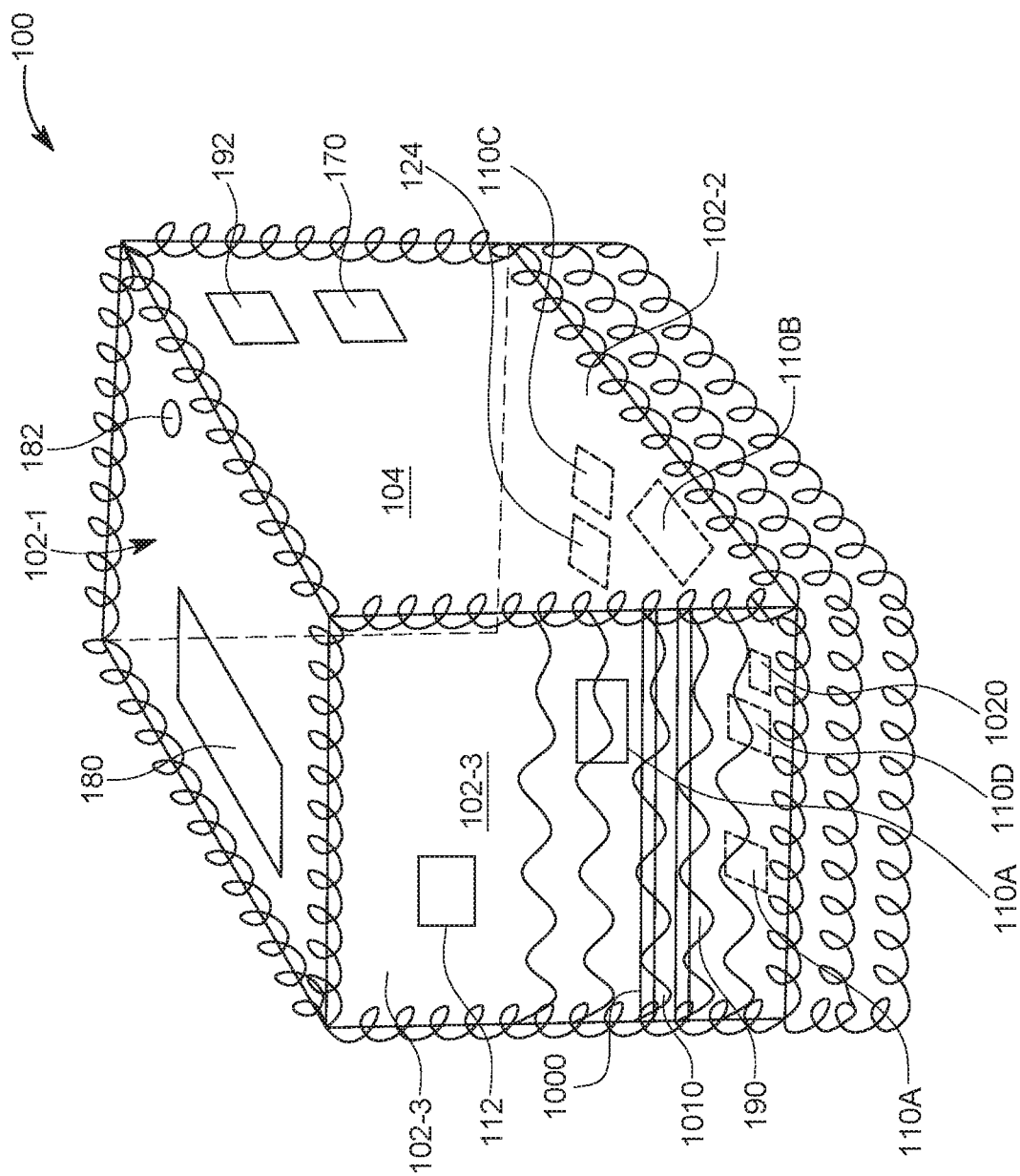
FIG. 10 shows the MD-IC device with the various elements disposed on various faces.

In one embodiment, because the MD-IC device is in constant contact with the water, a separate reservoir of cold water is not needed for dissipating the heat generated by the system. Micro-channels 1000 in the PDMS encapsulation 190 may be are fabricated using $CO_2$ laser ablation which are then capped with another flat PDMS layer 1010, as shown in FIG. 10. Test results for these channels show a ~9° C. reduction in temperature compared to a hot spot with no embedded microfluidic channels in its PDMS encapsulation layer. In one application, the $CO_2$ laser has a 75 W maximum power and achieves a resolution of 200 μm. The laser is moved with a speed of 2 mm/s, power of 0.75 W and a z-height of 1 mm along the existing PDMS layer to obtain the PDMS micro-channels with a 250 μm width. FIG. 10 also illustrates a possible configuration of the device 100, having the following sensors: the temperature sensor 110A (for example, one installed on the base face 102-2 for measuring the water temperature, and one installed on a side face 102-3 for measuring the air temperature), the pH level sensor 110B installed on the base face 102-2, the salinity sensor 110C, also installed on the base face 102-2 for measuring the salinity of the water, the ammonia sensor 110D installed on the base face 102-2 for measuring the amount of ammonia in the water, an air monitoring sensor 112 also installed on a side face, a solar panel installed on the top face 102-1, the LED 182 installed on the top face 102-1, the processor 124 installed on the inner side of the bottom face 102-2, the antenna 170 installed on a side face, and the communication unit 192 also installed on the side face. The memory and battery are not shown in the figure, but they may be located anywhere in the internal chamber 104.

Figure 11A:
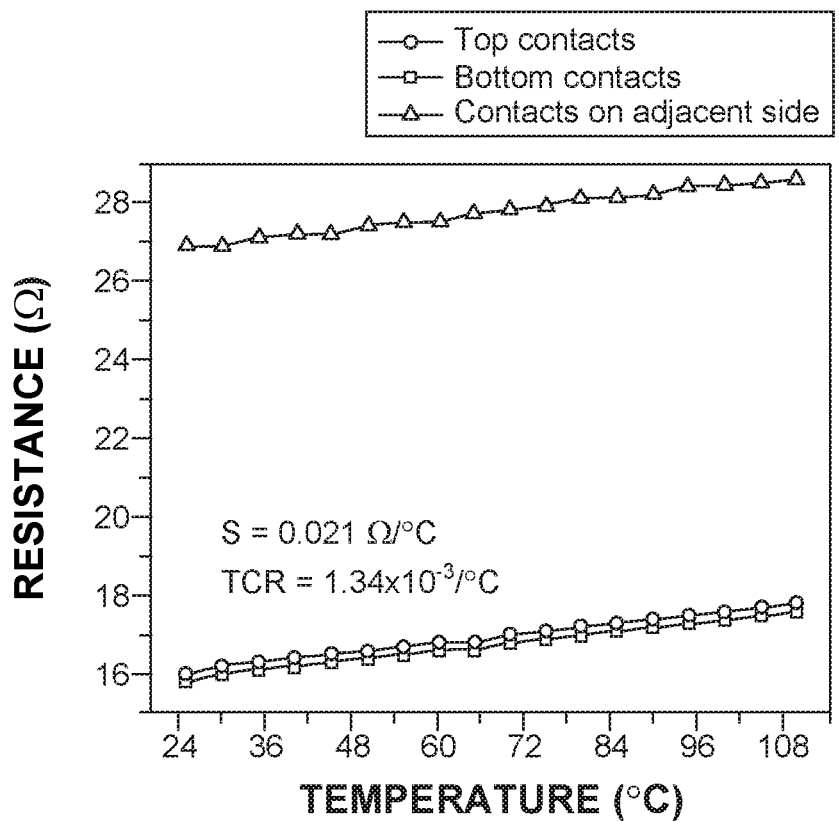
FIGS. 11A to 11D illustrate the results of the various tests applied to the sensors of the MD-IC device.

The obtained MD-IC device 100 was tested to confirm its reliable operation, and the different embedded sensors and electronics were characterized as now discussed. In addition, multiple reliability tests were conducted including un-biased highly accelerated stress test (μHAST), high temperature storage test (HTS) and environmental tests. The temperature sensor 110A is characterized by measuring the patterned metal resistance at different temperatures. A sensitivity of $0.021\Omega/°$ C. and a temperature coefficient of resistance (TCR) of $1.34 \times 10^{-3}/°$ C. were obtained as illustrated in FIG. 11A. The same measurements were conducted when probing the sensor from the back face (through the via) and from the interlocks on an adjacent face; upward shifts of $0.2\Omega$ and $11.1\Omega$ are observed, respectively, which is due to the added resistance of the metal contacts, however almost the same sensitivity is preserved.

Figure 11B:
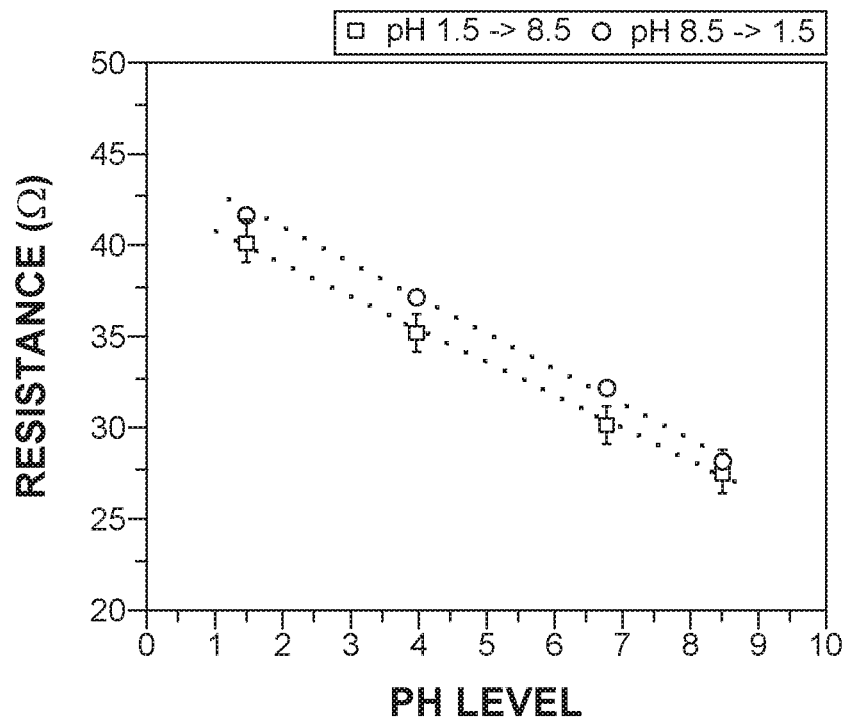

The pH level sensor 110B, which is based on a graphene monolayer, shows a reduced resistance in solutions with a higher pH level, as illustrated in FIG. 11B. The pH sensor was tested when exposed to solutions with a pH going from 1.5 to 8.5 (acid to alkaline) and vice versa, from 8.5 to 1.5 (alkaline to acid). A small hysteresis is observed as expected. In fact, the sensing mechanism in graphene is known to be nonfaradaic (capacitive), which means that charges do not transfer across the graphene/solution interfacial boudary (no redox reaction). Rather, the development of an adlayer occurs that changes the interfacial surface and results in a "doping effect." Owing to the nonfaradaic nature, where no exchange of charges occurs, charges are highly reversible (reversible adsorption), and as a result, when going from acidic to alkaline solutions and vice versa, a negligible hysteresis is expected. Moreover, the adsorbed $OH^-$ ions (in alkaline solution) are found to induce a larger conductivity in graphene than $H_3O^+$ ions (in acidic solution), which is consistent with the measured smaller resistance of graphene at higher pH levels.

Figure 11C:
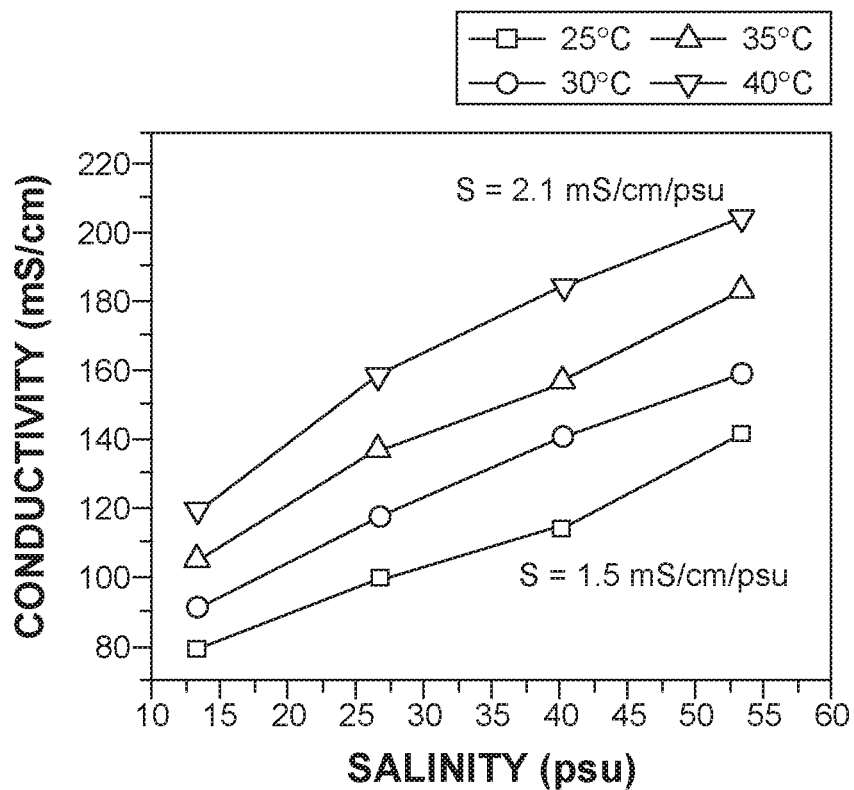

The salinity sensor 110C is based on conductivity measurements in order to measure the concentration of different undesirable salt ions in the fish farming ponds. Traditionally, a salinity sensor is based on a simple design with two electrodes separated by a specific distance. In the present salinity sensor, interdigitated electrodes are used instead of parallel electrodes. In fact, interdigitated electrodes enable a smaller cell factor which is needed for measuring low levels of conductivity. The results show that the conductivity of the saline solution increases with a higher concentration of salt and with the temperature. In fact, at higher concentrations of salt, more ions (anions and cations) are introduced into the solution, which contribute to the conductivity of the current. For the present tests, table salt with different concentrations is diluted in DI water, thus, $NaCl \rightarrow Na^+ + Cl^-$. At higher temperatures, the ions in the solution (anions and cations) gain more energy and move faster, resulting in an increase in the measured conductivity as illustrated in FIG. 11C. Therefore, the measurement of both salinity and temperature of the water is needed to extract the correct salinity level.

In one embodiment, the salinity sensor's operation is based on the measurement of the electrical conductivity of the water between the metallic electrodes. The electrical conductivity is defined by the multiplication of the conductance by the cell factor. The cell factor depends on the geometry of the sensor, where smaller values are required to sense and measure smaller concentrations of salinity. For fish farming ponds applications, where the acceptable range of water salinity is between 20 to 150 μS/cm, a cell factor of $0.1$-$0.5$ cm$^{-1}$ is required. The fabricated salinity sensor is based on the resistance measurement between platinum interdigitated electrodes with a spacing of 1 mm. The interdigitated electrodes design is chosen as it improves the sensitivity of the device and enables a lower cell factor for the same spacing when compared to the 2-electrodes design. The obtained cell factor is extracted by normalizing the measured conductance of ultrapure water to the measured conductivity using a commercial salinity sensor. Platinum is used as the sensor material due to its high-resistance to corrosion characteristic.

The ammonia concentration is measured using a 3D graphene foam-based sensor 110D. The 3D graphene foam is used as the sensing medium for ammonia. The graphene foam is induced by laser ablation of a 120-μm-thick polyimide sheet using a $CO_2$ laser with a power of 2.85 W and height of 3 mm. The obtained graphene foam is then transferred onto PDMS by spin coating the PDMS polymer on it and curing it at 60° C. for 2 hours. The PDMS is then stripped off of the polyimide sheet to obtain the ammonia sensors on the PDMS substrate. Both square and spiral designs were studied in terms of sensitivity and response time. It is found that the spiral structure with a higher surface area-to-volume ratio enables the sensor to be more efficient in absorbing the ammonia, resulting in a faster response and higher sensitivity.

Figure 11D:
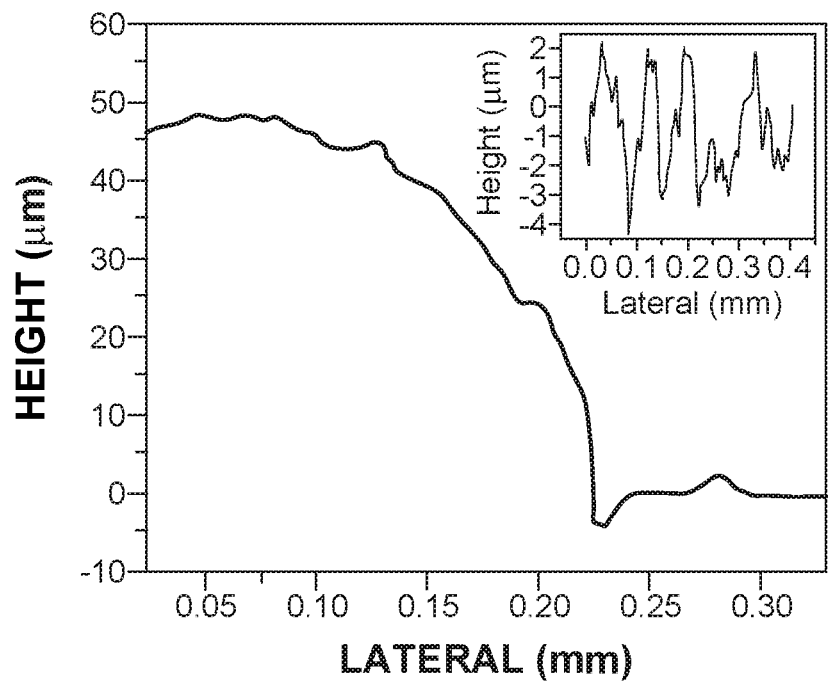

Graphene generally shows p-type characteristic under ambient conditions due to the electron extracting nature of oxygen and water functionalities. This means that electrons in the graphene are the minority carriers while the holes are the majority ones. The $NH_3$ molecules have strong electron-donor properties and are physically adsorbed on the graphene surface. Once the $NH_3$ molecules are adsorbed, the electron charge is partially transmitted to the graphene surface, and the holes in graphene are trapped in the electrostatic gravity of the electrons. As a result, the mobility of the hole carriers is reduced, causing an increase in the resistance of the sensor. Note that the exposure of the graphene to the ammonia at ambient conditions for long durations does not functionalize the graphene with nitrogen, which could otherwise affect the reliability of the device. The functionalization of the graphene requires exposure to a high energy and chemically active nitrogen such as annealing the graphene at high temperatures (≥300° C.) in $NH_3$ ambient and for long durations (several hours) or exposure to ammonia plasma. Moreover, the employed graphene has a porous 3D foam structure with a thickness of around 50 μm, as shown in FIG. 11D, with an RMS roughness of around 4 μm. It has been reported that a defective graphene shows a higher adsorption energy and charge transfer than its pristine graphene counterpart. The used 3D foam graphene is defective as confirmed by the broad Raman peaks (not shown), which enhances the response characteristic of the sensor.

The recovery behavior of the graphene foam was studied by exposing the sensor to a solution of ammonium hydroxide with a concentration of 7% $NH_3$ for around 15 min, then immediately dipping it in deionized (DI) water. A cycling test up to 4 cycles was conducted on the sample with the spiral design. The results show that once the sensor detects the ammonia and the $NH_3$ molecules are adsorbed on the surface of the graphene, the resistance is increased until it reaches a plateau, allowing a reliable reading of the sensor. Then, when the sensor is immediately placed in DI water, its resistance does not return back to its initial value. Instead, it shows a shift that becomes larger as the number of the $NH_3$ exposure cycles is increased, suggesting that residual ammonia molecules did not desorb completely from the sensing device.

Moreover, the results show that the recovery characteristic is slow (~10 min) which is in agreement with the reported recovery behavior of ammonia gas sensors based on graphene. This can be due to the large thickness and porosity of the 3D graphene, where some $NH_3$ residual molecules are left on the surface after the tested ammonia solution is replaced with deionized water. To solve this issue, heat is introduced during the desorption process (80° C.) to assist the complete recovery of the sensing element. In fact, it has been previously confirmed that introducing heat/annealing during the recovery period enhances the desorption characteristic of the adsorbates from the graphene. The results show that the resistance of the graphene sensor reduces until it reaches its initial state, when the sensor is heated. The desorption process takes around 10 min. Even when the sample is placed back at the room temperature in the DI water, the sensor continues to show the same initial resistance, which confirms that the $NH_3$ molecules are completely desorbed from the surface of the graphene.

Therefore, in the proposed MD-IC device, a heater 1020 is fabricated on the bottom face (inner side) 102-2 with the ammonia sensor 110D, as shown in FIG. 10. The heater 1020 is designed and fabricated by, for example, sputtering 1 μm of copper on the inner side of the bottom face 102-2. When biased with 3 V, the heater 1020 gets heated up to 80° C. within seconds. It is noted that the microcontroller 124 provides an output of 3.3 V on its output pins, which is suitable for triggering the fabricated heater 1020. Also note that 80° C. is considered as a low temperature, which should not cause any damage to any of the embedded sensors or devices of the device 100.

Thus, adding the heater 1020 is suggested in the final MD-IC device 100, which can be achieved by programming the embedded microcontroller 124 with a corresponding algorithm that performs the following steps: when the system detects an unacceptable ammonia level in the fish farming pond, a message is sent to the farmer. Next, the heater is triggered by the microcontroller in order to heat up the ammonia sensor and reset it to its initial resistance value. The process which consists of a) heating, b) recovery and b) cooling down is expected to take around 15-20 min in total, because the heating process is very fast (less than 20 s) while the recovery process takes around 10 min. In addition, the silicon face 102-2 with the water quality sensors is in direct contact with the cold water in the pond, which assists the heat dissipation and cooling down process. Therefore, during this "RESET" period, the output from the rest of the water quality sensors can be either neglected, because they might be affected by the generated heat, or their output can be corrected taking into consideration the temperature provided by the temperature sensor. Once the temperature sensor detects the last-recorded temperature value before triggering the heater (which means that the heat is fully dissipated and the system is cooled down), the ammonia sensor is considered as reset and all the water quality sensors can be back to normal operation.

Figure 12:
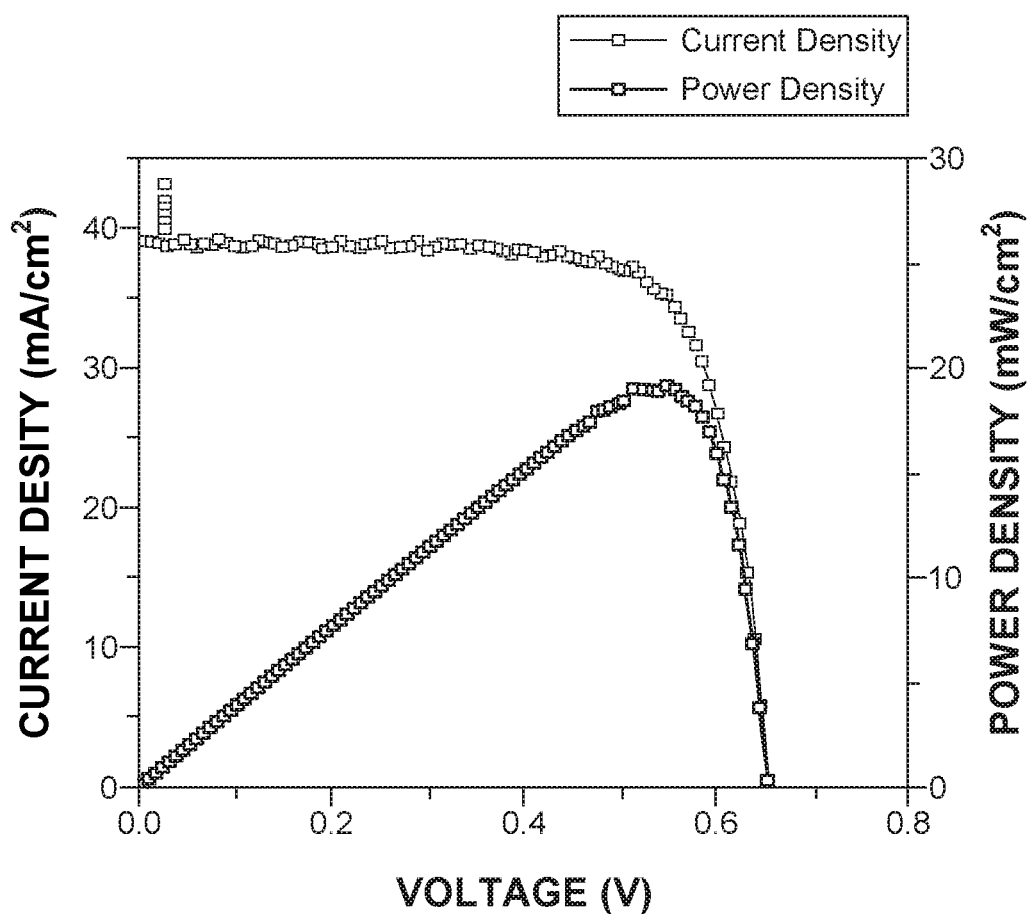
FIG. 12 shows results obtained when characterizing a solar panel placed on a surface of the MD-IC device.

The embedded monocrystalline silicon solar cell 180 was characterized using a solar simulator under 1 Sun AM 1.5G, and the measured efficiency of the solar cells was found to be about 19%, with a current density ($J_{sc}$) of about 39 mA/cm$^2$, an open circuit voltage ($V_{oc}$) of about 0.64 V, and a fill factor of about 75.8, as illustrated in FIG. 12.

As a result, a complete multi-sensory system 100 with energy harvesting/storage devices, data management circuitry and data transmission has been described above and the tests performed on its components show that this device is working and reliable. The measured data may be synchronously sent to a remote phone, in a wireless manner. In fact, the output of the various sensors discussed above could be connected to the input pins of the microcontroller, which would read and process the data based on the programmed algorithm (i.e. equations, correction factors, sensors sensitivities, etc.). In one application, the data collected by the temperature and salinity sensors are synergistically sent, via the Bluetooth Low Energy unit 192 to the mobile phone. The unit 192, which can be any communication unit, may be located inside the chamber 104. FIG. 10 also shows the antenna 170 and the LEDs 182. The LED 182 may be configured to illuminate following a certain pattern, when the measured parameter is higher than a given threshold, to send a visual signal to the farmer.

Figure 13A:
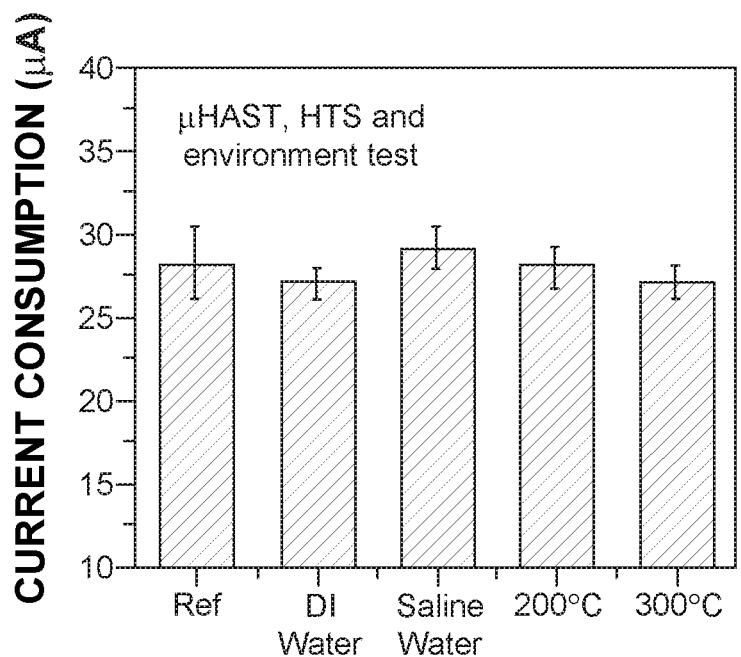
FIGS. 13A and 13B show test results of the microcontroller devices embedded in the MD-IC system when exposed to various ambient conditions.
Figure 13B:
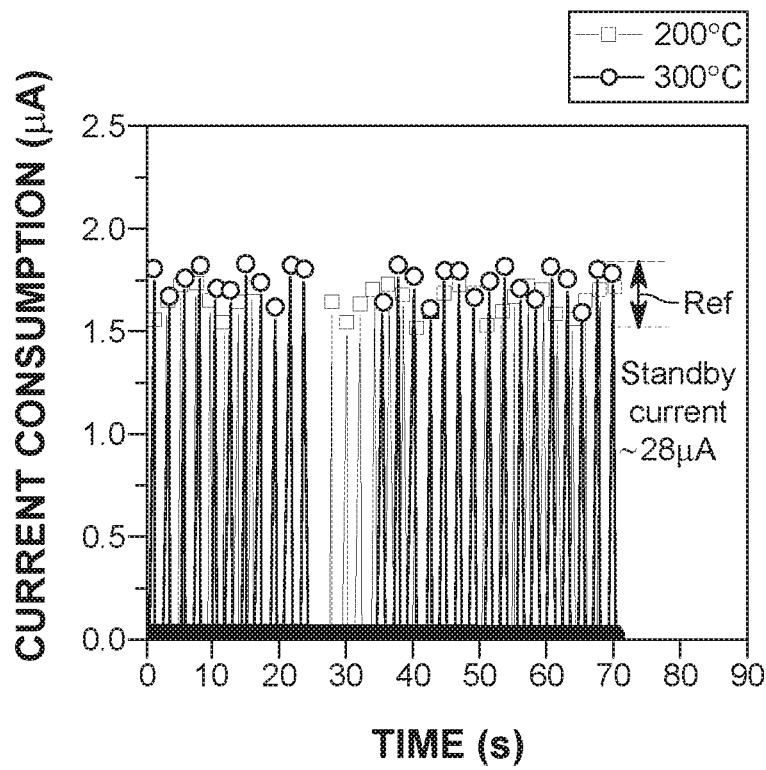

The MD-IC device 100 also passed component-level reliability tests including the µHAST at 200° C. and 300° C. at 60% RH humidity for 48 hours as shown in FIG. 13A, the HTS at 200° C. and 300° C. for 48 hours as shown in FIGS. 13A and 13B, and environmental tests (immersion in DI and saline waters) for 48 hours, as also shown in FIG. 13A. In fact, a DC test was conducted on the microcontroller to measure the current draw during the standby mode, after performing the reliability tests. The measured current consumption was similar to those obtained in the existing, which confirms that there were no defects in the multilayered PDMS layer causing any leakage of the fluids into the device. Moreover, although the maximum allowed storage temperature of the microcontroller IC is 150° C., FIG. 13B shows that the current consumption during the standby mode (leakage current) did not increase after the exposure of the embedded microcontroller IC to elevated temperatures, which suggests that the system could sustain harsh environment conditions. In addition, the poor thermal conductivity of the PDMS considerably reduced the exchange of the thermal energy across the encapsulation constituents. This was confirmed using infrared thermal imaging. As a result, if one side of the MD-IC device 100 gets heated up (e.g., the side with the encapsulated antenna gets heated up due to the sun exposure), the adjacent sides will experience a strongly attenuated effect due to the low thermal conductivity of the PDMS layer, which would otherwise result in faulty readings from the sensors.

Figure 14:
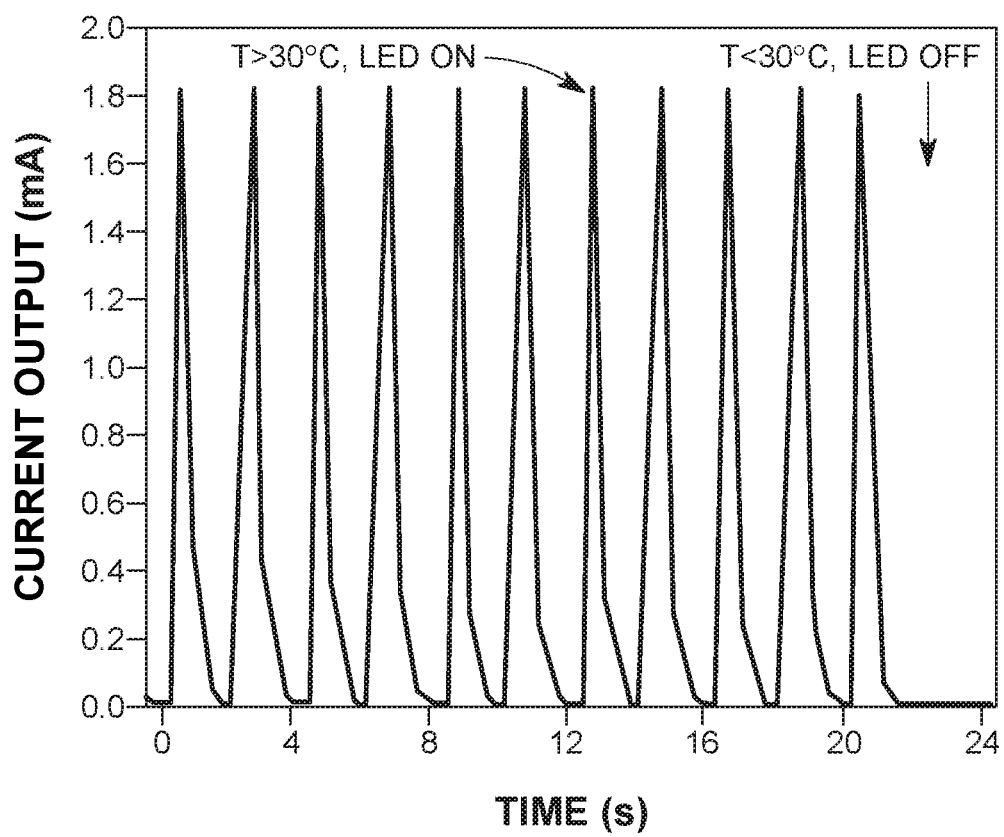
FIG. 14 shows test results when the MD-IC device is exposed to a high temperature.

A system-level reliability test was also performed on the cubic standalone device 100 where the embedded LED shines light as the device's temperature rises above a threshold value, for example 30° C. This is achieved by programming the microcontroller input and output pins connected to the temperature sensor and LED, respectively, and the results are shown in FIG. 14. Note that in this test, the sensors are integrated on various sides of the device and all faces of the cubic device include the effect of the side interconnects and TSVs. The MD-IC device 100 passed the system-level reliability test when the microcontroller current output received by the LED is similar to the existing data in the art.

The embodiments discussed above can be combined in any way as long as the MD-IC device 100 is able to measure water (or other fluid) and/or air parameters, and transmit them in a wireless manner to an outside device (smartphone, server, etc.). The device is also configured to float in water so that at least one face of the device is submerged in water for achieving a good interface between the water monitoring sensors and the water to be monitored. The design could be changed to enable the full immersion of the system depending on the application. A complete, small and lightweight IoT multi-sensory device 100 for simultaneous air and water-quality monitoring based on the MD-IC technology is thus demonstrated. The device integrates thin-film components on semiconductor substrates, which enables the integration and packaging of high density and high performance heterogeneous devices. In the demonstrated cubic MD-IC device 100, the water quality sensors may be embedded on a single outer face, which is in constant contact with water while the remaining outer faces include air quality sensors in addition to solar cells for energy harvesting and an antenna for wireless data-transfer. On the inner faces, data management circuitry and solid-state battery are embedded. To enable the system to float on the surface of the water with the same orientation, an asymmetric PDMS encapsulation may be used or each face is configured with the same sensors. The encapsulation assists in waterproofing the internal chamber in which the electronic devices such as the microcontroller and memory are placed, and in addition, it improves the mechanical resilience of the device. As a result, the farmer can easily deploy the MD-IC device by throwing it into the water, which will autonomously adjust its orientation owing to the PDMS encapsulation design. In one application, microfluidic channels in the PDMS encapsulation layer are used to dissipate the heat generated within the device. The device is configured to provide real-time monitoring results to the farmer. The MD-IC device may be used in IoT applications and can be further enhanced by integrating higher-efficiency III-V solar cells and additional water and air quality sensors, for example, optical sensors could be embedded on the outer vertical faces, in order to detect the deposition of any solid pollutant on the surface of the water such as plastic bag, cans, etc.

The MD-IC technology used for the device 100 is not a combination of two existing technologies, system-on-chip (SoC) and system-in-package (SiP), but instead it combines the benefits of both technologies, as now discussed. The Moore's law drives the SoC technology. This technology was preferred by multiple IC manufacturers for several years because it is able to achieve systems with high performance and a small form factor, low power consumption in addition to high density integration. The key enablers for this approach include the advances in lithography technique, and enhanced materials combinations in addition to the introduction of larger wafers. Even though SoC shows several benefits, however, it is restricted to a single wafer process. As a result, systems with restricted functionalities or a poorer performance of multiple electronic devices are obtained. Additionally, the SoC technology faces several challenges such as 1) extended design times as a result of the complex integration schemes which require multiple lithography masks, 2) high fabrication charges, and 3) designs verifications.

The SiP technology, on the other hand, is advantageous over the SoC technology by being capable of integrating heterogeneous chips with multiple functionalities (such as Bluetooth, antennas, imaging and so on) into a single package to achieve a full system. Moreover, the SiP technology, which consists of integrating different electronic devices on a PCB, has advantages over the SoC technology with regard to 1) less complex designs and therefore a lower number of masks would be needed, 2) faster implementation, and 3) larger memories integration. Nevertheless, the SiP technology is considered as a packaging technology rather than as an integration technology. In addition, its performance is generally restricted to the CMOS characteristics, which might not be ideal for specific devices, in addition to being very bulky compared to the SoC technology.

The MD-IC device 100 discussed herein uses a novel integration and packaging technique by taking advantage of a multi-dimensional integration of thin-film elements to merge the benefits of the SoC and SiP technologies. The MD-IC delivers a comprehensive system with multi-functionalities and a small form factor instead of the bulky printed-circuit-board employed by the SiP technology. Although both the SoC and SiP systems may include three dimensionally integrated devices, however, the MD-IC technology overcomes 1) the restricted functionality of the SoC technology, and 2) the bulky dimensions and inefficient area consumption of the SiP technology.

Thus, the MD-IC device 100 proves to be a more cost-effective solution then the existing devices because of one or more of the following features: (1) it uses both faces of the substrate for the devices integration, (2) it uses single-side polished substrates instead of double-side polished substrates, and thus, the devices that are based on different active materials than the substrate would be integrated on the unpolished side, (3) high-performance electronics can be fabricated on the different sides separately (no need for additional expensive lithography masks to integrate all of the devices on the same substrate as in SoC, (4) every single side can be based on a different substrate material (i.e., Si, Ge, GaAs, etc.) to boost the performance of the overall integrated circuit, (5) every side of the MD-IC device can be tested separately before merging them into a complete system which further increases the yield, and (6) previously reported IoT systems for water quality in fisheries are too bulky and require installation by experts, which increases the total cost compared to the MD-IC device, which can be deployed easily by the farmers.

Figure 15:
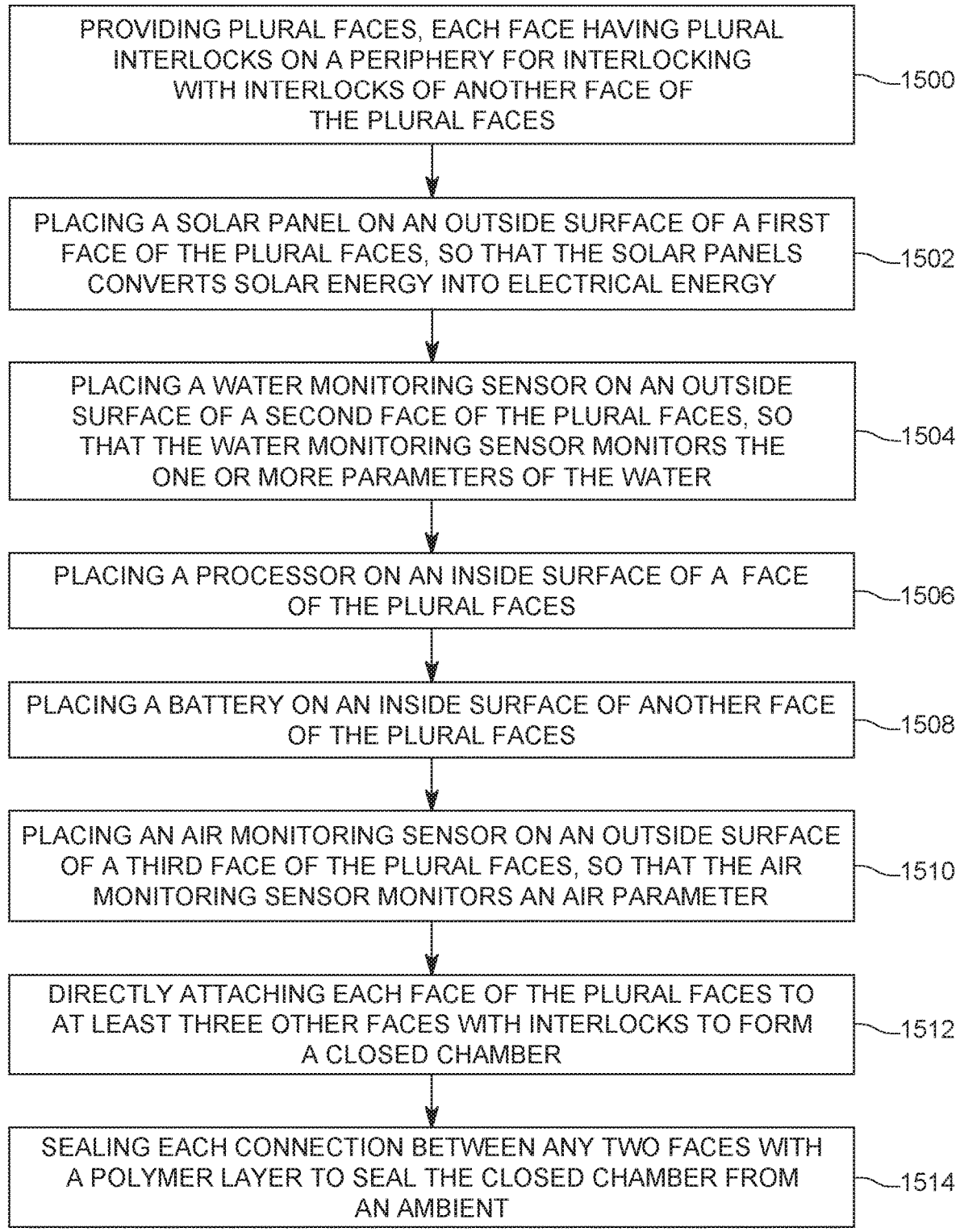
FIG. 15 is a flow chart of a method for making the MD-IC device.

A method of manufacturing the MD-IC device 100 that monitors one or more parameters in water is now discussed with regard to FIG. 15. The method includes a step 1500 of providing plural faces 102, each face 102-$i$ having plural interlocks 140 on a periphery for interlocking with interlocks 140 of another face of the plural faces 102-$i$, a step 1502 of placing a solar panel 180 on an outside surface 102A of a first face 102-1 of the plural faces 102, so that the solar panel 180 converts solar energy into electrical energy, a step 1504 of placing a water monitoring sensor 110 on an outside surface 102A of a second face 102-2 of the plural faces 102, so that the water monitoring sensor 110 monitors the one or more parameters of the water, a step 1506 of placing a processor 124 on an inside surface of a face of the plural faces, a step 1508 of placing a battery 120 on an inside surface of another face of the plural faces, wherein the battery 120 is configured to receive the electrical energy from the solar panel 180 and to provide the electrical energy to the processor 124 and the water monitoring sensor 110, a step 1510 of placing an air monitoring sensor 112 on an outside surface of a third face 102-3 of the plural faces 102, so that the air monitoring sensor 112 monitors an air parameter, a step 1512 of directly attaching each face of the plural faces 102 to at least three other faces with interlocks 140 to form a closed chamber 140, and a step 1514 of sealing each connection between any two faces with a polymer layer to seal the closed chamber 140 from an ambient.

The disclosed embodiments provide a MD-IC device that includes plural water and air monitoring sensors, together with a power source, processor and communication components for sending the measured data to an operator of a pond, while floating freely on the water of the pond. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A multi-dimensional integrated circuit (MD-IC) device for monitoring one or more parameters of a fluid, the device comprising:
   plural faces, each face having plural interlocks extending from a periphery of the face for interlocking with corresponding interlocks of another face of the plural faces;
   the plural faces are mechanically attached to each other and electrically connected through the interlocks to form a closed chamber;
   an energy harvester placed on an outside surface of a first face of the plural faces, so that the energy harvester converts solar energy into electrical energy;
   a fluidic monitoring sensor placed on an outside surface of a second face of the plural faces, so that the fluidic monitoring sensor monitors the one or more parameters of the fluid;
   a processor placed within the closed chamber; and
   a battery placed within the closed chamber and configured to receive the electrical energy from the energy harvester and to provide the electrical energy to the processor and the water monitoring sensor.

2. The device of claim 1, wherein the fluidic monitoring sensor includes:
   a pH sensor;
   a temperature sensor;
   a salinity sensor; and
   an ammonia sensor.

3. The device of claim 1, further comprising:
   an air monitoring sensor located on an outside surface of a third face of the plural faces.

4. The device of claim 3, further comprising:
   an antenna located on an outside of the chamber; and
   a communication unit located inside the chamber and configured to transmit data to an external device through the antenna.

5. The device of claim 4, further comprising:
   a light emitting device located on the first surface and configured to illuminate following a certain pattern when a value of the measured parameter is higher than a given threshold.

6. The device of claim 1, wherein each face of the plural faces is mechanically and electrically connected to at least three other faces of the plural faces through the interlocks.

7. The device of claim 1, further comprising:
   a layer of a polymer located at interfaces between the plural faces to seal the closed chamber.

8. The device of claim 7, wherein the layer of polymer does not cover the fluidic monitoring sensor.

9. The device of claim 7, wherein the closed chamber is a cube, the first face is a top face, the second face is a bottom face, and an amount of the polymer layer on the bottom face is larger than on each of the other faces so that MD-IC device floats in the fluid with the bottom face in full contact with the fluid.

10. The device of claim 7, wherein the layer of polymer has micro-channels so that the fluid enters through the micro-channels to cool off the closed chamber.

11. The device of claim 1, wherein the closed chamber is a pyramid or a sphere.

12. The device of claim 1, wherein each face is made of a semiconductor material and each face has semiconductor devices on both the internal and external surfaces.

13. The device of claim 12, wherein the internal surface of the semiconductor material is polished and the external surface of the semiconductor material is not polished.

14. The device of claim 12, wherein the first face has a substrate made of a first semiconductor material and the second face has a substrate made of a second semiconductor material, which is different from the first semiconductor material, and wherein the interlocks are metalized for conducting electrical signals from one face to another face of the plural faces.

15. A multi-dimensional integrated circuit (MD-IC) device for monitoring one or more parameters in a fluid, the system comprising:
    plural faces, each face having plural interlocks on a periphery for interlocking with corresponding interlocks of another face of the plural faces;
    the plural faces are attached to each other through the interlocks to form a closed chamber;
    an energy harvester is placed on an outside surface of a first face of the plural faces, so that the energy harvester converts solar energy into electrical energy;
    a fluidic monitoring sensor is placed on an outside surface of a second face of the plural faces, so that the fluidic monitoring sensor monitors the one or more parameters of the fluid;
    an air monitoring sensor is placed on an outside surface of a third face of the plural faces, so that the air monitoring sensor monitors an air parameter, wherein the third face is mechanically connected to both the first face and the second face; and
    a polymer layer externally covering connections between the plural faces to seal the closed chamber from ambient,
    wherein the polymer layer on the second face is thicker than on the first and third faces so that the third face is a bottom face and stays in contact with the fluid, the first face is a top face and exposes the energy harvester to sun, and the third face is a side face that exposes the air monitoring sensors to air.

16. The device of claim 15, wherein each face is made of a semiconductor material and the first and second faces have semiconductor devices on both the internal and external surfaces.

17. The device of claim 16, wherein the internal surface of the semiconductor material is polished and the external surface of the semiconductor material is not polished.

18. The device of claim 16, wherein the first face has a substrate made of a first semiconductor material and the second face has a substrate made of a second semiconductor material, which is different from the first semiconductor material.

19. The device of claim 15, further comprising:
    micro-channels formed in the polymer layer for cooling.

20. A method of manufacturing a multi-dimensional integrated circuit (MD-IC) device that monitors one or more parameters in a fluid, the method comprising:
    providing plural faces, each face having plural interlocks on a periphery for interlocking with corresponding interlocks of another face of the plural faces;
    placing an energy harvester on an outside surface of a first face of the plural faces, so that the energy harvester converts solar energy into electrical energy;
    placing a fluidic monitoring sensor on an outside surface of a second face of the plural faces, so that the fluidic monitoring sensor monitors the one or more parameters of the fluid;
    placing a processor on an inside surface of a face of the plural faces;
    placing a battery on an inside surface of another face of the plural faces, wherein the battery is configured to receive the electrical energy from the energy harvester and to provide the electrical energy to the processor and the fluidic monitoring sensor;
    placing an air monitoring sensor on an outside surface of a third face of the plural faces, so that the air monitoring sensor monitors an air parameter;
    directly attaching each face of the plural faces to at least three other faces with the interlocks to form a closed chamber; and
    sealing each connection between any two faces with a polymer layer to seal the closed chamber from an ambient.

* * * * *